United States Patent
Tonhauser et al.

(10) Patent No.: US 11,471,706 B2
(45) Date of Patent: Oct. 18, 2022

(54) POLYMER FOR TREATING HAIR

(71) Applicant: BASF SE, Ludwigshafen (DE)

(72) Inventors: Christoph Tonhauser, Ludwigshafen (DE); Veronique Schwartz, Ludwigshafen (DE); Sebastian Enck, Jakarta (ID); Peter Nesvadba, Basel (CH); Petra Keie, Ludwigshafen (DE); Antonietta Mauri, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 232 days.

(21) Appl. No.: 16/629,333

(22) PCT Filed: Jul. 13, 2018

(86) PCT No.: PCT/EP2018/069068
§ 371 (c)(1),
(2) Date: Jan. 8, 2020

(87) PCT Pub. No.: WO2019/016088
PCT Pub. Date: Jan. 24, 2019

(65) Prior Publication Data
US 2021/0137816 A1    May 13, 2021

(30) Foreign Application Priority Data
Jul. 18, 2017   (EP) .................................... 17181841

(51) Int. Cl.
| | | |
|---|---|---|
| *A61Q 5/00* | (2006.01) | |
| *A61Q 5/06* | (2006.01) | |
| *A61Q 5/12* | (2006.01) | |
| *A61K 8/41* | (2006.01) | |
| *A61K 8/81* | (2006.01) | |
| *C08F 220/58* | (2006.01) | |
| *C08F 8/32* | (2006.01) | |
| *C08F 226/10* | (2006.01) | |

(52) U.S. Cl.
CPC .................. *A61Q 5/12* (2013.01); *A61K 8/41* (2013.01); *A61K 8/8158* (2013.01); *A61K 8/8182* (2013.01); *A61K 8/8188* (2013.01); *A61Q 5/002* (2013.01); *A61Q 5/06* (2013.01); *A61K 2800/884* (2013.01); *C08F 8/32* (2013.01); *C08F 220/585* (2020.02); *C08F 226/10* (2013.01); *C08F 2800/10* (2013.01); *C08F 2810/50* (2013.01)

(58) Field of Classification Search
None
See application file for complete search history.

(56) References Cited

U.S. PATENT DOCUMENTS

| | | |
|---|---|---|
| 3,533,417 A | 10/1970 | Bartoszewicz et al. |
| 9,095,518 B2 | 8/2015 | Pressly et al. |
| 2003/0143175 A1 | 7/2003 | Samain et al. |
| 2013/0272981 A1 | 10/2013 | Nguyen et al. |
| 2018/0105620 A1* | 4/2018 | Chang ...................... C08F 8/34 |

FOREIGN PATENT DOCUMENTS

| | | |
|---|---|---|
| DE | 1023561 B | 1/1958 |
| DE | 102004024509 A1 | 12/2005 |
| EP | 0736297 A2 | 10/1996 |
| EP | 1893694 A2 | 3/2008 |
| EP | 2454328 A2 | 5/2012 |
| EP | 2606095 A1 | 6/2013 |
| WO | WO-2013/050547 | 4/2013 |
| WO | WO-2015/036553 | 3/2015 |
| WO | WO-2016/074986 | 3/2016 |

OTHER PUBLICATIONS

European Search Report for EP Patent Application No. 17181841.2, dated Jan. 29, 2018, 3 pages.
Kitano et al., PH-Responsive release of fluorophore from homocysteine-carrying polymerized liposomes, Macromolecules, 23(7):1958-1961 (1990).
Espeel et al., One-pot multi-step reactions based on thiolactone chemistry: A powerful synthetic tool in polymer science, European Polymer Journal, 62:247-72 (Jan. 2015).
International Application No. PCT/EP2018/069068, International Search Report and Written Opinion, dated Sep. 10, 2018.

* cited by examiner

*Primary Examiner* — Jyothsna A Venkat
(74) *Attorney, Agent, or Firm* — Marshall, Gerstein & Borun LLP

(57) ABSTRACT

The present invention relates to a polymer comprising repeating units derived from at least one first monomer (monomer A) which is a molecule comprising a thiolactone ring and an ethylenically unsaturated, polymerizable double bond, and at least one second monomer (monomer B) which is N-vinyl pyrrolidone. Furthermore the present invention relates to a modified polymer, the structure of which is identical to the structure of the said polymer apart from the only difference, which is that all or at least some of the thiolactone moieties of the said polymer are modified by opening the thiolactone ring with a substance selected from the group consisting of ammonia, a primary amine, 2-amino-1-ethanol and L-lysine, wherein the N-atom of said substance is binding to the carbonyl group of the opened thiolactone ring. Furthermore, the present invention relates to a process for making the modified polymer and to the use of the polymer or of the modified polymer for treating hair.

6 Claims, No Drawings

POLYMER FOR TREATING HAIR

CROSS-REFERENCE TO RELATED APPLICATIONS

This application is the U.S. National Stage application of International Patent Application No. PCT/EP2018/069068, filed Jul. 13, 2018, which claims the benefit of European Patent Application No. 17181841.2, filed Jul. 18, 2017.

The present invention relates to a polymer comprising repeating units derived from at least one first monomer (monomer A) which is a molecule comprising a thiolactone ring and an ethylenically unsaturated, polymerizable double bond, and at least one second monomer (monomer B) which is N-vinylpyrrolidone. Furthermore the present invention relates to a modified polymer, the structure of which is identical to the structure of the said polymer apart from the only difference, which is that all or at least some of the thiolactone moieties of the said polymer are modified by opening the thiolactone ring with a substance selected from the group consisting of ammonia, a primary amine, 2-amino-1-ethanol and L-lysine, wherein the N-atom of said substance is binding to the carbonyl group of the opened thiolactone ring. Furthermore, the present invention relates to a process for making the modified polymer and to the use of the polymer or of the modified polymer for treating hair.

Hair care products can be grouped in a) short-term hair care products and b) permanent or long-term hair care products. Short-term hair care products result in an effect that lasts until the hair is washed. E. g. conditioning shampoos or hair conditioners contain substances that are deposited on the hair during the washing process (shampoos) or after the washing process (hair conditioners are usually applied after washing the hair). Substances deposited on the hair can achieve effects like improved combability of the hair and other effects summarized under the term conditioning. Permanent or long-term hair care products result in effects that survive, at least partially, the washing of the hair.

Current permanent hair modifications involve straightening, coloring, bleaching as well as permanent wave treatments, most of which rely on chemical hair modification and result in a permanent damage on the keratinous fiber surface (cuticle). Most of the commercially available repair treatments do not offer acceptable solutions on the long-term since most of the commercially available conditioning products are based on physical interactions with the keratinous fiber and can thus be washed out after usage.

Known hair treatments such as coloring, bleaching, straightening or permanent wave treatments are based on chemical and/or thermal modifications of the hair fiber, which lead to permanent damage of the cuticle. For example, bleached hair strands undergo oxidative cleavage of disulfide and hydrophobic thioester surface groups as well as a loss of complete cuticles from the surface, which results in increased surface roughness, corroded edges and a softer cortex.

Known hair care products can address and temporarily fix these deficiencies by either smoothing the cuticle surface with a (in some cases crosslinked) polymeric film or by repairing disulfide bonds through interaction with small functional molecules. However, most of the current polymeric products which are commercially available rely on physical interactions with the keratinous fiber and do not last permanently. Proof of fixation over several washing cycles has been only shown in the case of hair dying technologies.

Therefore, there is a need for permanent or long-term hair modifications with reduced damage to the cuticle of the hair.

Redox chemistry on hair utilizing the cystine/cysteine-residues of the keratinous fiber is well known for creating permanent waves. In the standard process at hair dressers cystine moieties are reduced with ammonium thioglycolate to cysteine moieties and after shaping of the hair cysteine moieties are oxidized to cystine moieties with hydrogen peroxide to reform the disulfide bonds in the hair structure. It is a harsh process which damages the hair structure, especially the cuticle.

Besides the permanent wave treatment only few other examples are known using the cystine/cysteine-residues in keratinous fibers for permanent modification of the hair.

Small organic molecules can be used to repair the hair structure by combining cysteine residues with each other. This is disclosed in U.S. Pat. No. 9,095,518 B2.

WO 2013/050547 discloses the use of hydrophobic and cationic modified disulfides for conditioning of hair.

EP 1 893 694 A1 discloses disulfide hair dyes to obtain a permanent hair coloring.

EP 2 606 095 A1 discloses a polymeric hair dye with disulfide moieties which are covalently bound to the polymer which results in a hair dye technology with improved washing fastness.

EP 0 736 297 A1 discloses a cysteine-silicon polymer for treating keratin substrates. The low molecular weight of the polymer allows penetration into hair and removal of water leads to further polymerization/crosslinking of the silicon and thus to strengthening of the hair.

DE 102004024509 discloses the strengthening of hair structure using a polycondensation product of cystine and succinyl chloride in the permanent wave treatment.

US2003143175 A1 discloses a protective coating on the hair surface via covalent linkage of two complementary functional polymers, which are applied together in a cosmetic composition.

The teachings described in the previous paragraphs are limited to only a few single applications (e.g. hair dying and hair strengthening). In addition, in many cases a pretreatment of the keratin substrate with a reducing agent is mandatory for the described materials and processes.

The problem underlying the present invention is to provide a substance that allows for permanent or for long-term hair treatment with which it is possible to modify the properties of the hair. This treatment shall result in low damage to the cuticle of the hair. This treatment shall be workable without a mandatory pretreatment of the hair with a reducing agent.

This problem is solved by the polymer according to the claims of the present document. This polymer can be modified by opening at least some of the thiolactone rings of the polymer. The modified polymer thus obtained can be used for treating hair.

The subjects of the independent claims of the present text are the subjects of the present invention. The subjects of the dependent claims are special embodiments of the present invention.

The term hair means human hair or animal hair. Preferably hair is human hair.

Hair styling comprises the treatment of hair, which results in strong setting properties, preferably low tackiness and preferably a good humidity resistance. In particular, the treatment helps to retain a certain shape and stability for a prolonged time against environmental conditions such as wind, humidity and temperature.

Hair conditioning is understood by those skilled in the art to mean the treatment of hair with caring so-called rinse-off formulations (i.e. formulations which are rinsed off) or so-called leave-on formulations (i.e. formulations which remain on the hair without being rinsed off), particularly with caring shampoos or conditioners. This treatment leads in particular to easier combability of the hair in the wet and dry state, both along the lengths and at the tips (detangability), to improved tactile properties such as smoothness, softness and suppleness and also to good hair shine, little electrostatic charge and good ease of styling. Overall, a cared-for and healthy overall condition of the hair is thus achieved by the conditioning.

Hair repair is characterized by a treatment with a rinse-off or leave-on formulation, which forms a coating on the hair, thereby reducing damage to the surface of the hair fiber and tips (anti-snap) and improving tactile properties such as smoothness, softness and suppleness. An antipollution effect on hair and skin is characterized by a treatment, which provides shielding against the impact of pollution such as dust and sand particles as well as UV irradiation.

The polymer according to the present invention and the modified polymer according to the present invention can be used in formulations comprising the polymer or the modified polymer and further components known as ingredients of cosmetic formulations. Some of these components known as ingredients of cosmetic formulations are disclosed in WO 2016/074986 on page 4, beginning with "Tenside", to page 15, line 2.

The current invention aims at long-term hair care innovations via covalent attachment of new polymers to the keratinous fiber. New polymers based on N-vinylpyrrolidone have been modified with a monomer containing a thiolactone ring (described as "the first monomer" or "monomer A" in the present text) to covalently interact with the cystine/cysteine-residues of the keratinous fiber via redox chemistry. This creates a permanent modification of the hair surface and leads to multiple applications in the Hair Care business. Variations of the polymer segments attached to the hair fiber allow for the tailor-made adjustment for specific applications in the hair care market (e.g. hair repair (antifrizz, antipollution), hair protection, hair styling, hair conditioning, volume control, volume creation).

The present invention relates to materials, compositions and methods for treating keratinous substrate to use disulfide bonds in hair or skin for the permanent modification of hair or skin surface by new polymeric materials.

The current invention aims at permanent or long-lasting hair care products via covalent attachment of new polymers to the keratinous fiber, making use of the thiol/disulfide redox chemistry of the cystine-rich cuticle.

The covalent interaction and attachment to the hair fiber is established via thiol/disulfide and/or disulfide exchange reaction of the S-containing building blocks with the cystine-rich cuticle. In contrast to current technologies, the concept allows for a universal attachment of a great variety of polymeric segments to the hair fiber as long as they can be modified with a monomer containing a thiolactone ring (described as "the first monomer" or "monomer A" in the present text). The invention can be used in the Hair Care market to introduce permanent properties to the hair by a new technology. Depending on the polymeric backbone, several subsegments are addressed such as hair styling (long-lasting styling, mild hair treatment, long-lasting straightening, volume creation and control), hair repair (antifrizz, antipollution, hair strength), hair conditioning (hair gloss, conditioning).

Damaged & virgin hair treated with thiol-modified PVP provides a smoother feeling, additional gloss and better combing properties for the user. In addition, hair treated with the modified polymers provides a better long-term stability of perceivable effects, which can be retained over several washing cycles.

It is an advantage of the polymer according to the present invention that it provides a moisturizing effect. A moisturizing effect is an effect that results in an improved retention of moisture or water in comparison to untreated hair (or hair treated with a benchmark substance). It can be determined by measuring the rate of loss of water from the treated hair tress in comparison with a standard under the same conditions. Furthermore, a moisturizing effect results in an enhanced uptake of moisture during a wash cycle. This can be determined gravimetrically in a direct comparison between treated hair and untreated/benchmark treated hair. Furthermore, a moisturizing effect results in the maintenance of a constant moisture/water content over time compared with untreated hair or a benchmark without becoming "frizzy" or "sticky". This can be characterized via hair volume measurements as wells as classic adhesion tests at the hair surface.

It is assumed that the presence of repeating units derived from N-vinylpyrrolidone are responsible for bringing about this moisturizing effect.

An advantage compared to existing products is the permanent character of the hair modification. The modification of the hair stays over a long period of time to create a long-lasting perceivable benefit for the user. Compared to known permanent hair care solutions the present invention can not only repair broken disulfide bonds in the hair structure (hair repair) but the invention is versatile. The cysteine/cystine hair chemistry can be used to introduce various polymeric building blocks to adjust the hair properties tailor-made for specific applications.

The First Monomer (Monomer A)

Monomer A is a molecule comprising a thiolactone ring and an ethylenically unsaturated, polymerizable double bond. Preferably the thiolactone ring is a ring of 5 atoms.

In one embodiment of the present invention monomer A has the following formula (I).

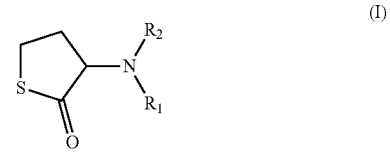

(I)

In formula (I) R1 is a group comprising an ethylenically unsaturated, polymerizable double bond and R2 is selected from the group consisting of H, C1-C6 alkyl and C1-C6 acyl. Alternatively, in formula (I) R1 and R2 form together a group comprising an ethylenically unsaturated, polymerizable double bond.

In one embodiment of the present invention, monomer A has formula (I), wherein R1 is selected from the group consisting of an allyl group, an acryl group (acryloyl group), a methacryl group, a vinyl phenyl group, a C1-C6 alkyl group which has attached to the C-atom that is the most remote to N, an acryl or a methacryl group and a —C(O)—O—R3—O—R4 group, wherein O—R3—O is derived from a C1 to C6 diol and R4 is acryl or methacryl, and wherein R2 is H.

In one embodiment of the present invention, monomer A has formula (I), wherein R1 and R2 form together with the N-atom to which they are attached a polymerizable maleinimide ring which may be substituted with one or two $CH_3$-groups.

In one embodiment of the present invention monomer A is N-homocysteine thiolactone methacrylamide.

The amount of monomer A in the polymer according to the present invention is not limited as long as repeating units derived from monomer A and from monomer B are present. In one embodiment of the present invention the amount of monomer A in the polymer is 1 to 10 mol-% with respect to the sum of the molar amounts of monomers A and B, preferably this amount is 2 to 8 mol-%, more preferably it is 3 to 7 mol-%.

The Second Monomer (Monomer B)

Monomer B is N-vinylpyrrolidone (more exactly named N-vinyl-2-pyrrolidone).

The amount of monomer B in the polymer according to the present invention is not limited as long as repeating units derived from monomer A and from monomer B are present. In one embodiment of the present invention the amount of monomer B in the polymer according to the present invention is 90 to 99 mol-% with respect to the sum of the molar amounts of monomers A and B, preferably this amount is 92 to 98 mol-%, more preferably it is 93 to 97 mol-%.

The Third Monomer (Monomer C)

Monomer C is any monomer comprising an ethylenically unsaturated, polymerizable double bond, wherein monomer C is different from monomer A and different from monomer B.

Throughout the whole of the present text the meaning of (meth)acrylate is that a species named (meth)acrylate can be an acrylate or a methacrylate.

In one embodiment of the present invention monomer C is selected from the group consisting of an alkyl acrylate having 4-21 carbon atoms and an alkyl methacrylate having 5-23 carbon atoms.

In one embodiment of the present invention monomer C is selected from the group consisting of acrylic acid, methacrylic acid, methyl acrylate, methyl methacrylate and C2-C10 alkyl (meth)acrylates.

In one embodiment of the present invention monomer C is selected from the group consisting of tert-butyl acrylate, tert-butyl methacrylate, 2-ethylhexyl acrylate, 2-ethylhexyl methacrylate, cyclohexyl acrylate and cyclohexyl methacrylate.

In one embodiment of the present invention monomer C is selected from the group consisting of an alkyl (meth)acrylate having 4-21 carbon atoms which optionally has one or more substituents selected from the group consisting of hydroxyl, amino and carbamoyl groups, oligoethylene ethers or heterosubstituted rings (the carbon atoms of the substituents are not included in said 4 to 21 carbon atoms).

In one embodiment of the present invention monomer C is selected from the group consisting of hydroxy ethyl (meth)acrylate, methyl polyethylene glycol (meth)acrylate, behenyl polyethylene glycol (meth)acrylate, 2-(2-oxooxazolidine-3-yl) ethyl (meth)acrylate, 2-carbamoyloxypropyl acrylate, 2-imidazolium-1-yl-ethyl methacrylate, 2-(2-oxopyrrolidine-1-yl) ethyl (meth)acrylate, tert-butylaminoethyl (meth)acrylate, 2-morpholinoethyl (meth)acrylate, (3,4,5-trihydroxy-6-methoxy-tetrahydropyran-2-yl) methyl acrylate, di methylaminoethyl (meth)acrylate and 2-(4-benzoyl-3-hydroxy-phenoxy)ethyl prop-2-enoate (Uvinul® 19 acrylate).

In another embodiment monomer C is selected from a group consisting of an ester of vinyl alcohol having 3-21 carbon atoms, preferably vinyl acetate.

In another embodiment monomer C is selected from the group consisting of an N-vinyl heteroaromatic compound and an allyl-heteroaromatic compound. Preferred embodiments in this group are pyridines, pyrimidines, pyrroles and imidazoles. More preferred embodiments in this group are 2-, 3- and 4-vinylpyridine, N-vinyl caprolactame, N-vinyl imidazole, N-vinylformamide and N-vinyl-N-methylacetamide.

In another embodiment monomer C is selected from the group consisting of an N-alkyl (meth)acrylamide having a C1-6 alkyl group, an N-acyl (meth)acrylamide having a C1-6 acyl group and an amino- or methyl-substituted aminoalkyl acrylamide. Preferred embodiments in this group are (meth)acrylamide, dimethyl acrylamide, dimethylaminoethyl acrylamide and diacetoneacrylamide In another embodiment monomer C is a ethylenically unsaturated cationic monomer with one or several quaternized nitrogen groups. Preferred embodiments in this group are quaternized N-vinyl imidazole or quaternized dimethylaminopropyl (meth)acrylate, wherein the counterions can be chloride, methyl sulfate or ethyl sulfate. The quaternization is preferably a methylation.

In another embodiment monomer C can have 2 to 6 ethylenically unsaturated polymerizable double bonds and is selected from a group consisting of an alkyl acrylate having 4-21 carbon atoms and an alkyl methacrylate having 5-23 carbon. Preferred embodiments in this group are diethylene glycol di(meth)acrylate, 1,4-butanediol di(meth)acrylate and polyethylene glycol di(meth)acrylate.

In another embodiment monomer C is an ethylenically unsaturated mono- or dicarboxylic acid. Preferred embodiments in this group are fumaric acid, maleic acid, crotonic acid, itaconic acid and cinnamic acid.

In another embodiment monomer C is selected from vinylaromatic compounds which contain one ethylenically unsaturated double bond and an aromatic ring system. Examples are styrene, α-methyl styrene or vinyl toluenes.

The amount of monomer C in the polymer according to the present invention is 0 to 10 mol-% with respect to the sum of the molar amounts of monomers A and B, preferably this amount is 0 to 5 mol-%, more preferably it is 0 to 2 mol-%.

Further Embodiments of the Polymer According to the Present Invention

In one embodiment of the present invention monomer A is N-homocysteine thiolactone methacrylamide and monomer B is N-vinylpyrrolidone and there is no monomer C.

In another embodiment of the present invention monomer A is N-homocysteine thiolactone methacrylamide, monomer B is N-vinylpyrrolidone and monomer C is selected from the group consisting of acrylic acid and methacrylamide.

N-homocysteine thiolactone methacrylamide can be made as described in "H. Kitano, H. Wolf, N. Ise, Macromolecules 1990, 23, 1958-1961."

The polymer according to the present invention can be made by conventional polymerization techniques.

EXAMPLES

N-homocysteine thiolactone methacrylamide was synthesized as described in "H. Kitano, H. Wolf, N. Ise, Macromolecules 1990, 23, 1958-1961."

Polymer Example 1: Synthesis of polyvinylpyrrolidone-N-homocysteine-thiolactone methacrylamide copolymer 400 g of 2-propanol were heated to 75° C. in a 2 liter reaction vessel, equipped with a stirrer and a condenser. 167.5 g N-vinylpyrrolidone and 12.5 g N-homocysteine thiolactone methacrylamide were dissolved in 150 g 2-propanol and constantly added to the preheated solvent within 4 hours. At the same time, 1.8 g of azobis-2-methyl-butyronitrile (Wako V59), dissolved in 100 g of 2-propanol, were constantly added within 4.5 h. Subsequently, the mixture was polymerized for another 2 hours and cooled down to room temperature. The product was subjected to steam distillation and stored in the form of an aqueous solution of 20 wt.-% at room temperature.

Polymer Example 2: Reactive activation of polyvinylpyrrolidone-co-poly-N-homocysteine thiolactone methacrylamide by aminolysis and labeling with fluorescent dye.

5 g of polyvinylpyrrolidone-N-homocysteine-co-poly-N-homocysteine thiolactone methacrylamide were dissolved in 15 g of dimethyl sulfoxide in a 50 mL 3-neck-flask, equipped with a stirrer, condenser and a nitrogen connection and mixed with 1 g of 2-aminoethan-1-ol and 20 mg of tris(2-carboxyethyl)phosphine hydrochloride. The mixture was stirred under nitrogen atmosphere for 2 hours at room temperature. Subsequently, 200 mg of fluorescein-O-acrylate were added and the mixture was stirred for another 4 hours at 40° C. under exclusion of light. The fluorescently-labeled polymer was purified via dialysis and stored in aqueous solution under exclusion of light.

Polymer Example 3 (a comparison example): Synthesis of fluorescently-labeled polyvinylpyrrolidone 209.5 g of N-vinylpyrrolidone, 0.5 g of ammonia and 790.86 g of water were heated to 75° C. in a 2 liter reaction vessel, equipped with a stirrer, a condenser and a nitrogen connection. In the meanwhile, 1.26 g of fluorescein-O-acrylate and 0.1 g of 2,2'-azobis(2,4-dimethylvaleronitrile) (Wako V65) were dissolved in 1.26 g acetone and added to the mixture at 50° C. The mixture was stirred for 1 hour under nitrogen flow when the temperature reached 70° C. The remaining initiator (0.1 g V65 in 1.26 g acetone) was added and the mixture was stirred for another hour. Finally, a last portion of 1.66 V65 in 4.88 g acetone was added and the mixture was stirred for another 30 minutes. Subsequently, the mixture was heated to 90° C. and further polymerized for 2 hours. 0.63 g of formic acid was added and the mixture was stirred for another 30 minutes before cooling down to room temperature. The pH was adjusted to 7 with ammonia and the polymer was purified via steam distillation. The final pH was adjusted to 8 with 25 wt.-% of sodium hydroxide solution.

Application Examples

For the following applications tests a "permanent lotion" with ammonium thioglycolate and a "fixation lotion" with hydrogen peroxide were used.

Solution A (Permanent Lotion): water, ammonium thioglycolate, ammonium bicarbonate, butylene glycol, propylene glycol, PEG-35 castor oil, ethoxydiglycol, Coceth-10, carnitine HCL, perfume, Polyquarterium-6, ammonium hydroxide, Quarternium-80, benzyl salicylate, linalool, citronellol, alpha-isomethyl ionone Solution B (Fixation Lotion): water, hydrogen peroxide, propylene glycol, PEG-35 castor oil, Laureth-4, PEG-40 hydrogenated castor oil, Coco-Betaine, phosphoric acid, creatine, perfume, Polyquarternium-35, salicylic acid, Sodium Cocoamphoacetate, butylphenyl methylpropional, linalool, alpha-isomethyl ionone, tetrasodium pyrophosphate, benzoic acid Application Example 1: Binding of polymers to hair that was pre-treated with Solution A Solution A was applied on blond hair (3 blond hair strands) at room temperature and incubated for 10 min. The hair strands were rinsed under tap water and the towel dried strands were treated each with the following polymer solutions (i) Polymer Example 2 (ii) Polymer Example 3 (iii) no polymer, at room temperature. The hairs strands were kept for 2 h at 70° C. and then rinsed. The towel dry strands were treated with Solution B at room temperature and kept at room temperature for 10 min. Then the strands were rinsed under tap water and dried for 12 h at room temperature. All hair strands were tested with respect to wash fastness (10× washed with shampoo).

Result: fluorescence spectroscopy pictures of all three hair strands were recorded. Only the thiol-containing polymer showed strong fluorescence after the wash fastness test proving the covalent and permanent modification of the hair surface.

Application Example 2: Binding of polymers to hair that was not pre-treated with Solution A Application Example 1 was repeated without treatment with solution A and without treatment with solution B.

Result: Identical results from fluorescence spectroscopy for of all three hair strands compared to application example 1.

This result indicates that the polymer according to Polymer Example 2 binds covalently to hair even without Solution A and without Solution B.

Apart from the evaluation with fluorescence spectroscopy the hair strands obtained in Application Examples 1 and 2 were also evaluated by colorimetric reflectance measurements. The results are summarized in the following table.

The colorimetric reflectance measurements result in a dE* value which was determined according to EP2454328B1. The colorimetric reflectance measurements were conducted with the following spectrophotometer: "Datacolor Spectraflash SF 450" equipped with a xenon light source filtered to D65 with a measurement geometry of diffuse illumination and 8° viewing. The measurements of the hair tresses were conducted directly on the measure head using a plate with an aperture (hole) of 6.6 mm. The measurements were conducted 8 times and the average values were used. Before the measurements, the spectrophotometer was calibrated using a black and a white standard provided by Datacolor. The measurement was carried out as described in EP 2 454 328.

The following table shows the results of color change compared to the hair strand (iii) of the application tests. A high number auf dE* shows a good washing fastness of the corresponding polymer and thus a permanent modification of the hair (this is the case for numbers 1 and 3).

| No. | Example | Hair type | Polymer | dE*-indicating washing fastness and thus covalent binding |
|---|---|---|---|---|
| 1 | Application Example 1 | Blond native | Polymer Example 2 | 44.4 |
| 2 | Application Example 1 | Blond native | Polymer Example 3 | 3.21 |
| 3 | Application Example 1 | Blond native | No polymer treatment | 1.22 |
| 4 | Application Example 2 | Blond native | Polymer Example 2 | 29.9 |
| 5 | Application Example 2 | Blond native | Polymer Example 3 | 9.0 |
| 6 | Application Example 2 | Blond native | No polymer treatment | 0.79 |

The colorimetric reflectance measurements confirm the results of the fluorescence spectroscopy measurements: the polymer according to Polymer Example 2 binds covalently to hair even without Solution A and without Solution B. The difference between the values 44.4 and 29.9 has no known significance.

The invention claimed is:

1. A polymer comprising
   one first monomer which is N-homocysteine-thiolactone methacrylamide and
   one second monomer which is polyvinylpyrrolidone.
2. The polymer according to claim 1, wherein
   the amount of one first monomer in the polymer is 1 to 10 mol-% and
   wherein the amount of second monomer in the polymer is 90 to 99 mol-%
   and wherein the amount of monomer C in the polymer is 0 to 10 mol-% with respect to the sum of the molar amounts of monomers A and B.
3. The polymer according to claim 1 wherein the amount of one first monomer in the polymer is 2 to 8 mol-%.
4. The polymer according to claim 1 wherein the amount of one first monomer in the polymer is 3 to 7 mol-%.
5. The polymer according to claim 1 wherein the amount of the second monomer in the polymer is 92 to 98 mol-%.
6. The polymer according to claim 1 wherein the amount of the second monomer in the polymer is 93 to 97 mol-%.

* * * * *